United States Patent [19]
Hermann

[11] Patent Number: 5,738,513
[45] Date of Patent: Apr. 14, 1998

[54] ARCHWIRE LOCKING DEVICE FOR ORTHODONTIC BRACKET

[76] Inventor: Lawrence Hermann, 180 W. End Ave., Apt. 28R, New York, N.Y. 10023

[21] Appl. No.: 555,775

[22] Filed: Nov. 9, 1995

[51] Int. Cl.[6] ............................................. A61C 3/00
[52] U.S. Cl. ............................................. 433/13
[58] Field of Search ........................ 433/8, 10, 11, 433/12, 13

[56] References Cited

U.S. PATENT DOCUMENTS

| | | |
|---|---|---|
| 3,477,128 | 11/1969 | Andrews . |
| 3,959,880 | 6/1976 | Andrews . |
| 4,103,423 | 8/1978 | Kessel ............................. 433/10 |
| 4,371,337 | 2/1983 | Pletcher . |
| 4,415,330 | 11/1983 | Daisley et al. . |
| 4,419,078 | 12/1983 | Pletcher ........................... 433/10 |
| 4,547,153 | 10/1985 | Taylor . |
| 4,634,662 | 1/1987 | Rosenberg ....................... 433/10 |
| 4,712,999 | 12/1987 | Rosenberg ....................... 433/11 |
| 4,786,252 | 11/1988 | Fujita .............................. 433/10 |
| 5,224,858 | 7/1993 | Hanson ........................... 433/10 |
| 5,275,557 | 1/1994 | Damon ............................ 433/10 |
| 5,322,435 | 6/1994 | Pletcher ........................... 433/11 |
| 5,474,445 | 12/1995 | Voudouris ........................ 433/10 |
| 5,516,284 | 5/1996 | Wildman ......................... 433/10 |

OTHER PUBLICATIONS

Article, "Frictional Forces with the Friction-Free Edgewise Bracket," Journal of Clinical Orthodontics, Inc., 1828 Pearl Street, Boulder, Colorado 80302, vol. XXVIII, No. 6, Jun., 1994.

Article, "Dr. G. Herbert Hanson on the SPEED Bracket," Journal of Clinical Orthodontics, Inc., 1828 Pearl Street, Boulder, Colorado, 80302, vol. XX, No. 3, Mar., 1986.

Advertisment For "Synergy—The Reduced Friction Appliance System."

Advertisment brochure, "The Activa advantage is 5×5 times better."

*Primary Examiner*—Nicholas D. Lucchesi
*Attorney, Agent, or Firm*—Gottlieb, Rackman & Reisman, P.C.

[57] ABSTRACT

An archwire locking device for an orthodontic bracket system is provided. The system includes a series of conventional edgewise brackets which engage the teeth of a patient by means of an adhesive which bonds the bracket to the tooth. Each bracket includes a laterally extending slot for selectively receiving an orthodontic archwire. The archwire locking device of the invention is used for maintaining the archwire within the laterally extending archwire slot of the bracket. The locking device is selectively moveable between a first locked position and a second unlocked position.

32 Claims, 8 Drawing Sheets

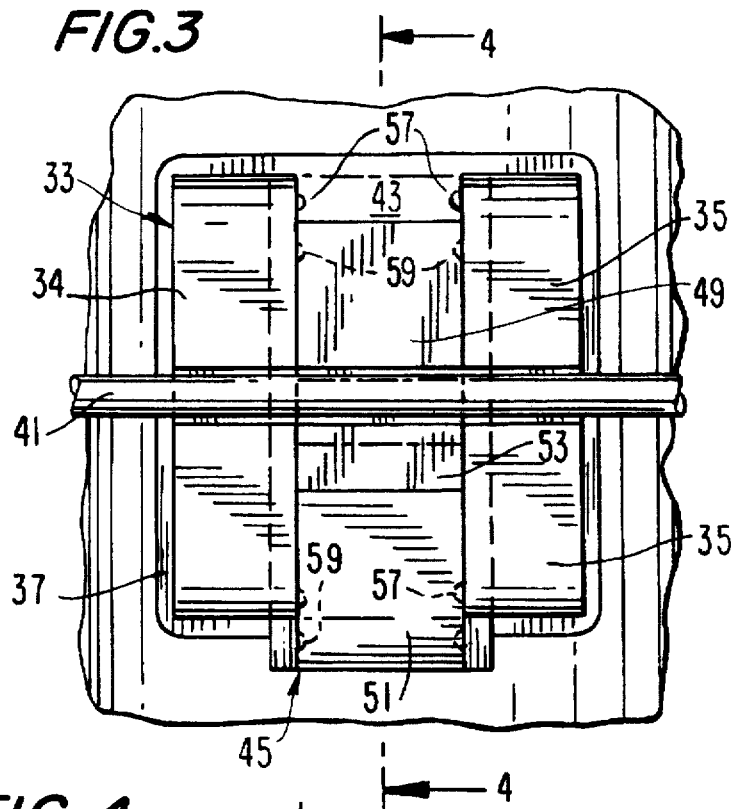
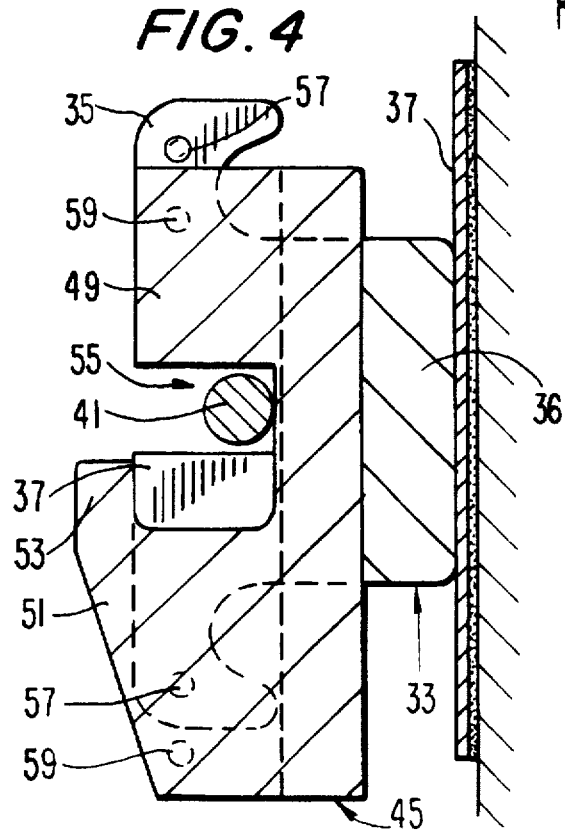
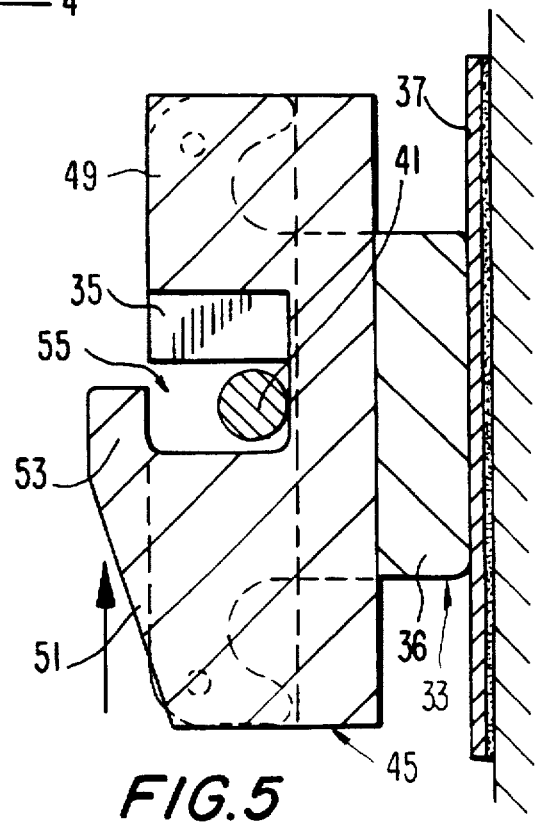

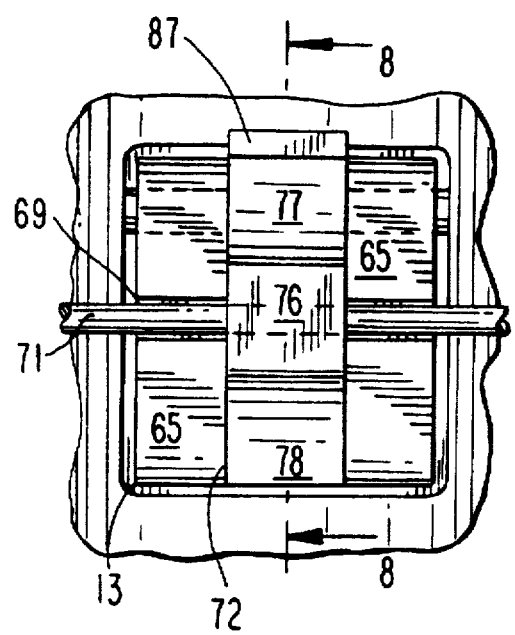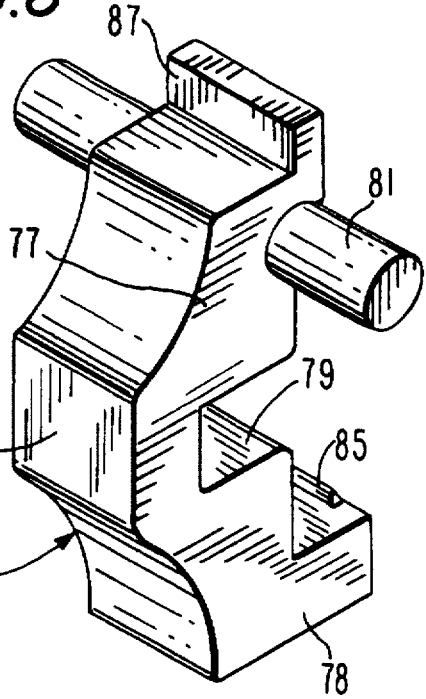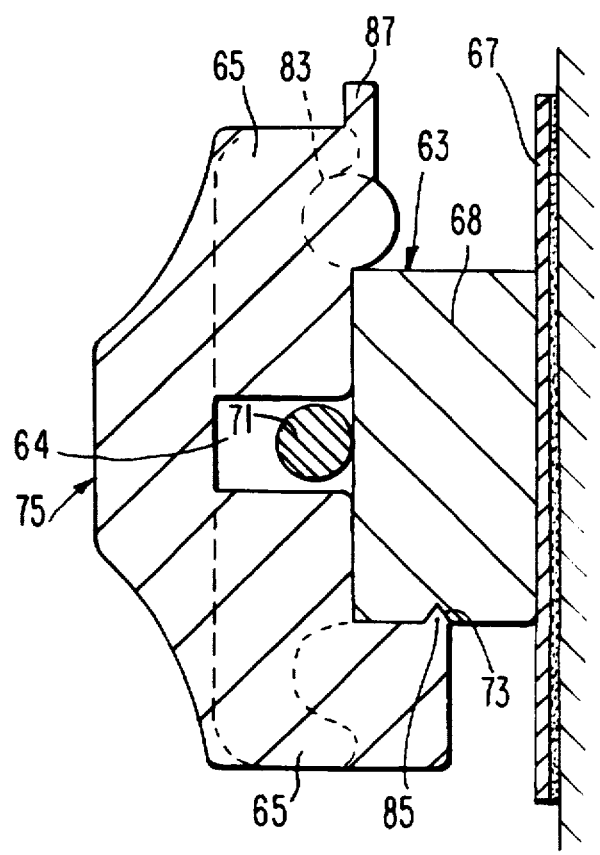

ARCHWIRE LOCKING DEVICE FOR ORTHODONTIC BRACKET

BACKGROUND OF THE INVENTION

The current practice of orthodontics requires the use of brackets which are bonded to the teeth, or which are welded to stainless steel bands that encircle each tooth and are cemented in position. Each bracket is then ligated to an orthodontic archwire, which is periodically changed during the orthodontic treatment process. In the first place, an archwire may be adjusted by the dental practitioner in order to cause movement of the patient's teeth. In addition, elastic bands, or elastic chains and springs, can be attached to the bracket in order to move the teeth to a desired position along the orthodontic archwire.

The most popular type of orthodontic bracket is known as an edgewise bracket, which was introduced by Dr. Edward Angle in about 1925. There are two basic types of edgewise brackets, a single width edgewise bracket in which the body is cut across by an archwire slot, and a twin edgewise bracket, as shown in use in FIG. 1. Approximately 95% of all brackets that are in use in orthodontic treatment are edgewise brackets, and of these, about 90% are twin edgewise brackets.

Twin edgewise brackets are generally divided between standard edgewise brackets and preadjusted edgewise brackets. A standard twin edgewise bracket has a separation between the mesial and distal wings that is at right angles to the archwire slot. Moreover, the general outline of such a bracket from the facial or buccal view is square or rectangular. A preadjusted edgewise twin bracket, on the other hand, in most instances, has a rhomboid or trapezoid shape when viewed from the facial or buccal surface. Moreover, the slot between the wings of a preadjusted edgewise twin bracket is at an angle to the archwire slot.

In all edgewise brackets, as alluded to above, the archwire has to be ligated to the bracket in order to hold the archwire in place. This requires the use of a steel ligature wire, which is placed under the wing tips and over the archwire that is in the archwire slot. The two ends of the steel ligature are twisted together and cut off, leaving a little excess length to be bent under the archwire and close to the body of the bracket in order to avoid irritating the patient's tissues. The most common method of holding the archwire in place is by using a very small elastomeric plastic "O" ring, identified as 29 in FIG. 1, which is stretched under wing tips 25 of bracket 23 and over archwire 31 along both sides of bracket 23.

Ligating the archwire with a steel ligature is both time consuming and difficult. Moreover, if the patient later chews sticky or hard foods, the ends of the twisted ligature often bend outward and irritate the dental tissue, usually requiring an emergency visit to the orthodontic practitioner. While elastic ligatures avoid this problem, and are easily applied, even by moderately skilled dental personnel, they are less than desirable, since they degrade quickly in the mouth, and over a short period of time, loose their elasticity, preventing them from fully engaging the archwire in the archwire slot.

Synthetic elastomeric ligatures are usually made of the same material as elastomeric chains, and each "link" in the chain is essentially the same dimension as a single elastomeric ligature. In an article entitled "Synthetic Elastomeric Chains: A Literature Review" by David L. Baty et al. in *The American Journal of Orthodontics and Dentalfacial Orthopractices* in June, 1994, it was found that elastomeric chains generally lost 50% to 70% of their initial elasticity during the first day of location. Moreover, it was further found that elastomeric chains retain only 30% to 40% of original elasticity at the end of three weeks, which is the usual interval between orthodontic appointments for a patient. Furthermore, like elastic chains, synthetic elastomeric ligatures quickly degrade in the mouth and accumulate debris. This creates an unhygienic situation and an unsightly appearance, requiring frequent replacement of them.

Various mechanical self-locking or self-ligated brackets have been developed in the past. These brackets in general have limited versatility and acceptance. As can be appreciated, the orthodontic practitioner is normally well trained in the use of traditional twin edgewise brackets, and has developed various techniques to correct severe rotation, tipping and other malpositions of the teeth using these brackets. Therefore, using a self ligating bracket instead of a conventional twin edgewise bracket is less than desirable. This is because such self-locking brackets are usually of the single width type and the dental practitioner will undoubtedly not have sufficient confidence that he can treat orthodontic cases with the same degree of perfection and ease as he could with a conventional twin edgewise bracket.

In addition, using a self ligating bracket is less than desirable because of the length of time (around two years) it takes to complete a standard orthodontic treatment. If the orthodontic practitioner uses a typical self-ligating bracket, and the results are not satisfactory, it may be necessary to remove the brackets from the patient's teeth, and replace them with the traditional twin edgewise type of bracket, which obviously is both time-consuming and costly.

Accordingly, the present invention enables the orthodontic practitioner to use a single or twin edgewise bracket, including a preadjusted edgewise bracket, yet still have the convenience and efficiency of a self-locking mechanism which can be easily removed as desired.

SUMMARY OF THE INVENTION

Generally speaking, in accordance with the invention, an archwire locking device for an orthodontic bracket system is provided. The system includes a series of conventional single or twin edgewise brackets, including pre-adjusted type edgewise brackets, which engage the teeth of a patient by means of an adhesive which bonds the bracket to the tooth. The preferred embodiment is for a twin edgewise bracket, and comprises a base which leads into a pair of wing tips extending along either side thereof, and which defines a longitudinal groove running between the pairs. Each of the pairs further defines a laterally extending slot for selectively receiving an orthodontic archwire.

The archwire locking device of the invention is used for maintaining an archwire within the laterally extending archwire slot of the bracket. The locking device is selectively moveable between a first locked position within the longitudinal groove disposed between the wing tip pairs of the bracket for capturing the archwire, and a second unlocked position away from the bracket groove.

In one embodiment, the locking device is slidably positioned within the longitudinal groove and includes a catch which holds the archwire in the archwire slot of the bracket. In a second embodiment, the locking device includes a pivot pin which enables the device to pivotally rotate between a locked position for capturing the archwire along the archwire slot of the bracket, and an unlocked position away from the archwire slot.

The locking device of the invention is both self-locking and removable. Moreover, one locking device may be interchanged for a second, depending upon the forces to be exerted upon the archwire. Furthermore, the inventive locking device is both aesthetic and hygienic.

Accordingly, it is an object of this invention to provide an archwire dental locking device for an orthodontic bracket system.

Still another object of the invention is to provide an archwire dental locking device which enables a dental practitioner to use standard or preadjusted edgewise brackets.

Yet another object of the invention is to provide an archwire dental locking device which is both hygienic and aesthetically pleasing.

A further object of the invention is to provide an archwire dental locking device which is easily removed and interchanged.

Another object of the invention is to provide an archwire dental locking device which at least partially engages the archwire of the orthodontic bracket system.

Still other objects and advantages of the invention will in part be obvious and will in part be apparent from the following description.

The invention accordingly comprises the device possessing the features, properties and relation of components which will be exemplified hereinafter, and the scope of the invention will be indicated in the claims.

BRIEF DESCRIPTION OF THE DRAWINGS

For a fuller understanding of the invention, reference is made to the following description, along with the accompanying drawings, in which:

FIG. 3 is a front or top plan view of the first embodiment of the inventive archwire locking device in an unlocked position within the dental bracket;

FIG. 4 is a cross-sectional view taken along line 4—4 of FIG. 3;

FIG. 5 is a cross-sectional view similar to FIG. 4, but showing the first embodiment of the inventive locking device in a locked position within the dental bracket;

FIG. 6 is a perspective view of a second embodiment of the dental locking device in accordance with the invention;

FIG. 7 is a front or top plan view showing the second embodiment of the inventive dental device in a locked position within a twin edgewise dental bracket;

FIG. 8 is a cross-sectional view along the line 8—8 of FIG. 7.

DETAILED DESCRIPTION OF THE PREFERRED EMBODIMENTS

Figure 1:
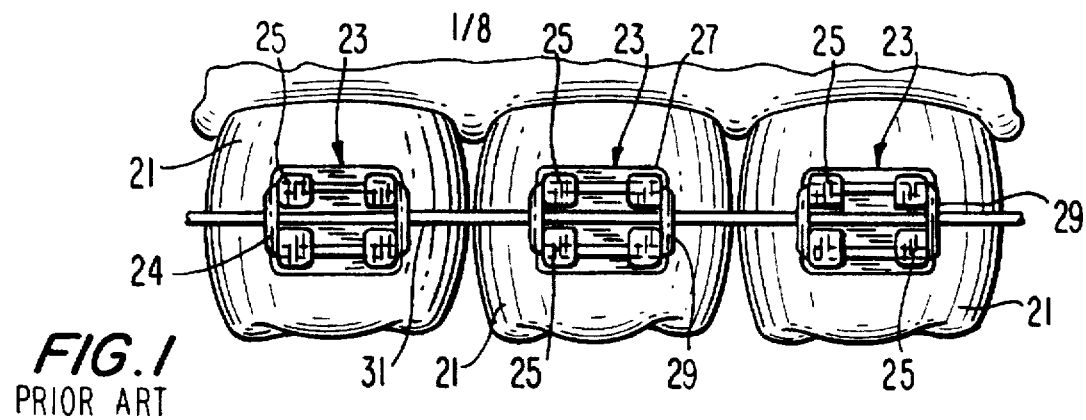
FIG. 1 is a top plan view of an orthodontic bracket system of the prior art which uses plastic "O" rings for holding the dental archwire in place.
Figure 2:
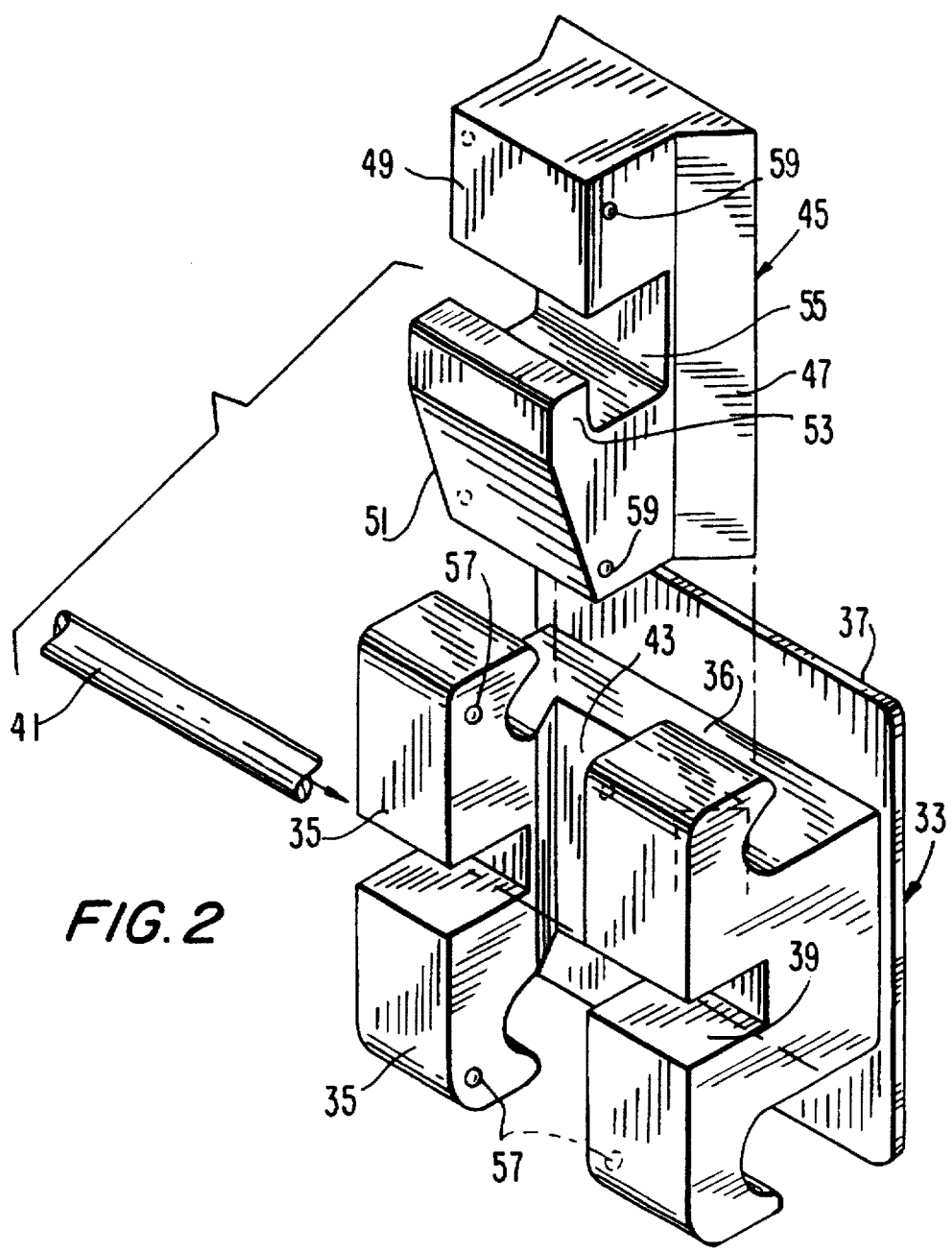
FIG. 2 is an exploded perspective view of an orthodontic twin edgewise bracket utilizing a first embodiment of the inventive archwire locking device.
Figure 9:
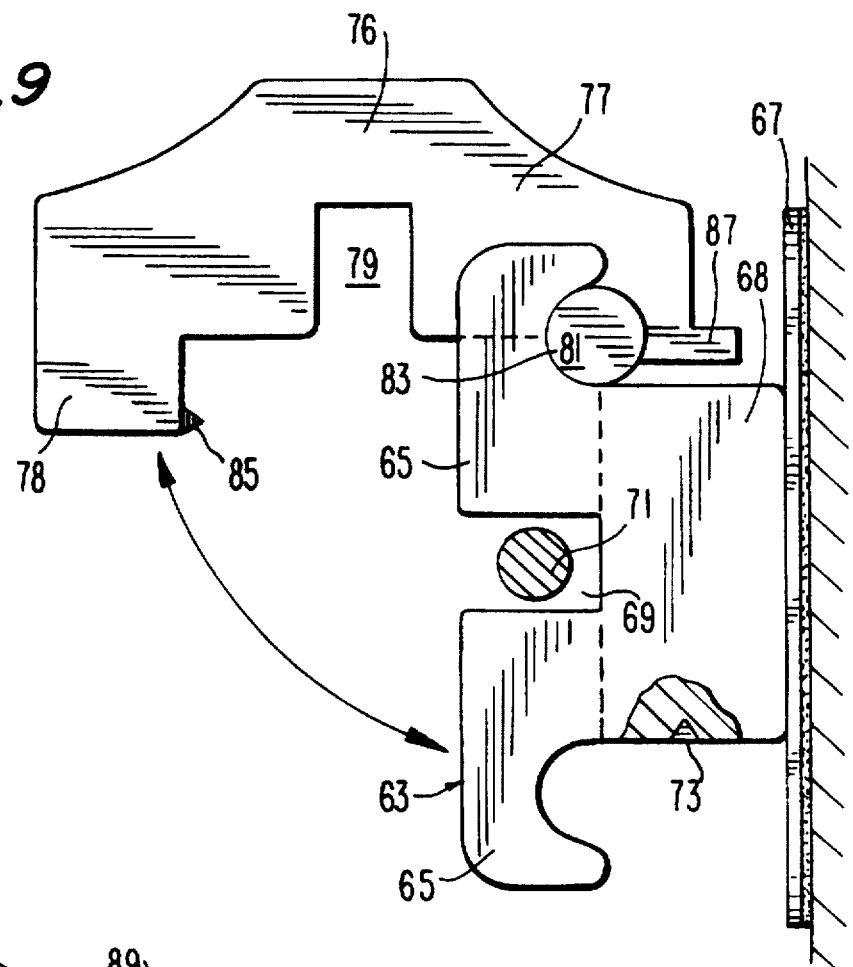
FIG. 9 is a side elevational view in partial cross-section showing the second embodiment of the dental locking device in an unlocked condition with respect to the dental bracket.

Referring first to FIG. 2, a first embodiment of an orthodontic bracket locking device in accordance with the invention, generally indicated at 45, is shown. Locking device 45 is used with an orthodontic twin edgewise bracket, generally indicated at 33. Bracket 33 includes a substantially planar base 36 and four projecting wing tips 35. Base 36 is fixed to a foil mesh pad 37 which is used for bonding bracket 33 to a tooth, as is well known in the art. Wing tips 35 define a longitudinally extending archwire slot 39 for receiving archwire 41 as shown. Wing tips 35 further define a laterally extending channel 43 which selectively receives locking device 45, as described below.

Locking device 45 comprises a base portion 47 with a pair of upright fingers 49 and 51 extending therefrom. Fingers 49 and 51 define a slot 55 therebetween for retaining archwire 41 when locking device 45 is mounted within bracket 33. Significantly, finger 51 includes a catch portion 53 extending partially over slot 55, which facilitates retention of archwire 41 therewithin.

As shown in FIGS. 3–5, locking device 45 is slid within channel 43 of bracket 33 in order to capture archwire 41. In FIGS. 3 and 4, locking device 45 is shown in an unlocked condition, whereas in FIG. 5, locking device 45 has been slid into a locked condition with respect to bracket 33. As can be appreciated, when locking device 45 is in a locked condition, buttons 57 formed along the inside surfaces of wing tips 35 are engaged within notches 59 formed along the outside of upright fingers 49 and 51 of locking device 45. Moreover, when locking device 45 is in a locked condition, archwire slot 39 is substantially aligned underneath catch 53, as best shown in FIG. 5.

When locking device 45 is positioned within channel 43 of bracket 33, such that it is in a locked condition (see FIG. 5), locking device 45 cannot be removed by archwire 41 pulling in a direction away from the facial or buccal surface of the tooth. Moreover, archwire 41 can also not move locking device 45 in a gingival or incisal direction due to the inner gingival and incisal surfaces of slot 39.

Locking device 45 holds archwire 41 within slot 39, even when the latter is moved in either a gingival or occlusal direction when device 45 is in a locked condition. In order to unlock archwire 41 from slot 39, locking device 45 is slid in a downward direction, as shown in FIG. 3.

Turning now to FIGS. 6–9, the second embodiment of the locking device of the invention is described and generally indicated at 75. Locking device 75 is used for retaining an archwire 71 within archwire slot 69 of a twin edgewise bracket generally indicated at 63. As before, bracket 63 includes a base 68 and four extending wing tips 65 which define both a longitudinal extending slot 69 for receiving archwire 71 and a laterally extending channel 72. A pad 67 is provided for facilitating attachment of bracket 63 to the patient's tooth.

Locking device 75 includes a bridge or body 76 which leads on either side into a pair of arms 77 and 78. Arm 78 includes a protruding lip 85 for selective engagement with a notch 73 formed in base 68 of bracket 63, as described below. Arm 77 is formed with a semi-circular cut-out 83 for fixedly retaining a pivot pin 81 therewithin, as shown in FIGS. 6 and 8. Arm 77 further includes an extending projection 87 depending away from pivot pin 81.

In operation, locking device 75 can rotate along pivot pin 81 fixed to arm 77 from a first unlocked condition (see FIG. 9) to a second locked condition (see FIG. 8). Pin 81 is selectively and freely removable from under wing tips 65 as is needed by the operator. Locking device 75 is formed with a retaining channel 79 located underneath bridge 76 which captures archwire 71 therewithin when locking device 75 is in a locked condition, as best shown in FIG. 8. When in a locked condition, lip 85 of arm 78 engages notch 73 formed within base 68 to ensure that locking device 75 is maintained within channel 72 formed between wing tips 65 of bracket 63.

Figure 10:
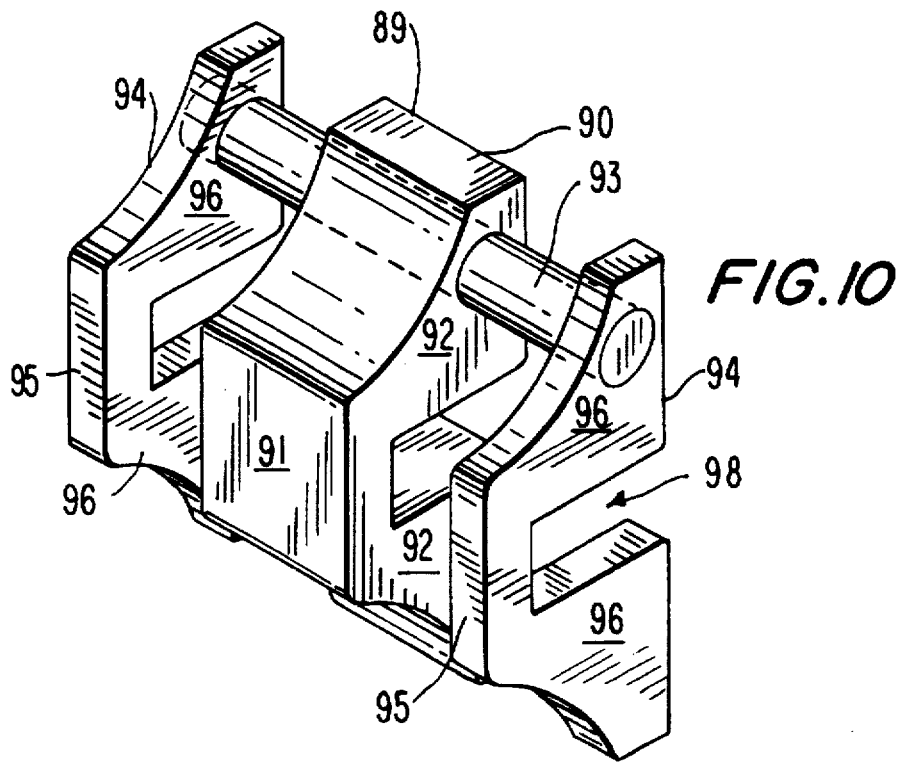
FIG. 10 is a perspective view of a third embodiment of a locking device in accordance with the invention.

Turning now to FIG. 10, a third embodiment of an archwire dental locking device is described and generally indicated at 89. Locking device 89 is similar to locking device 75 depicted in FIGS. 6–9 described hereinabove and includes a main locking member 90 comprising a bridge or body 91 and arms 92. One of arms 92 as shown is formed with an opening running therethrough for receiving a pivot pin 93 which extends on either side past member 90 and is fixed at either end to side locking arms 94.

Each of side locking arms 94 has a configuration similar to the configuration of main locking member 90, and each includes a body 95 and a pair of arm members 96. As shown, the same corresponding arm member 96 of each of side arms 94 is fixed to the ends of pivot pin 93. In addition, each of main locking member 90 and side locking arms 94 define a channel 98 running therethrough which is used to capture the dental archwire when dental locking member 89 is mounted appropriately over a dental bracket.

In use, side locking arms 95 are positioned along the outside mesial and distal edges of the wings of a conventional twin edgewise bracket. As before, main locking member 90 is mounted substantially along the laterally extending channel defined by the wing tips of the dental bracket so that channel 98 defined by member 90 and arms 94 can capture the dental archwire. As can be appreciated, each of member 90 and arms 94 can pivotally rotate together along pivot pin 93 in order to move locking device 89 from a first locking condition to a second unlocking condition in a manner similar to what is shown in the second embodiment depicted in FIG. 9.

Although not depicted in FIG. 10, each of locking member 90 and arms 94 may include a locking lip, similar to lip 85 depicted in the second embodiment shown in FIGS. 6–9, to facilitate the locking of locking device 89 over the dental bracket.

Figure 11:
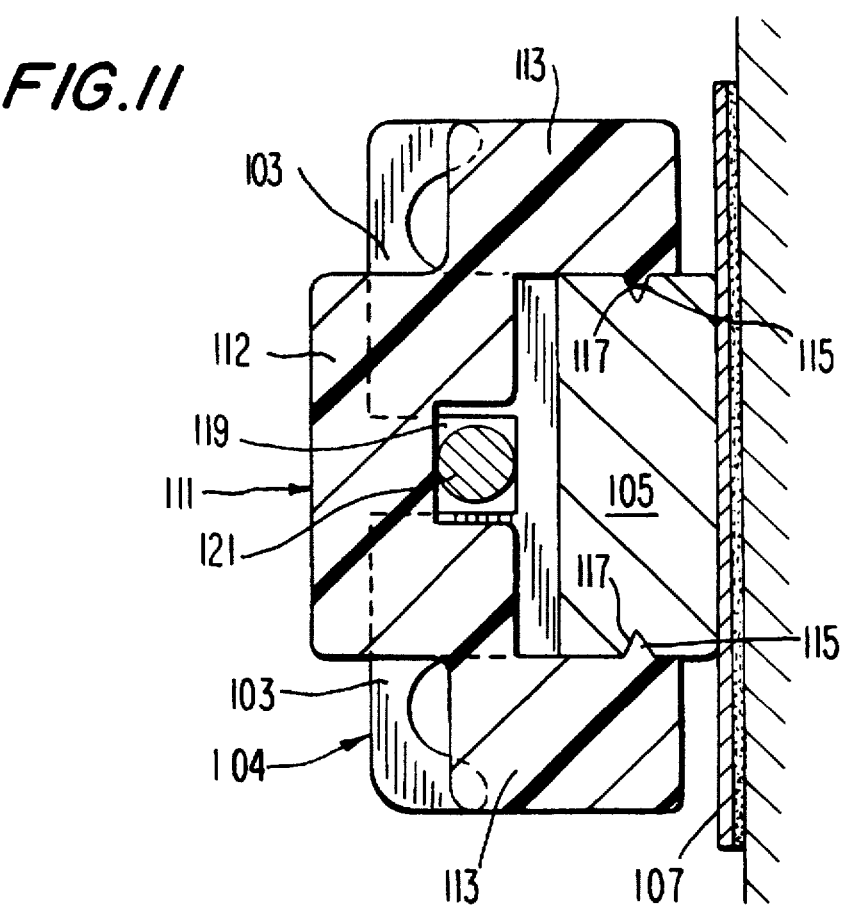
FIG. 11 is a side elevational view in cross-section showing a fourth embodiment of a dental locking device in accordance with the invention.

In FIG. 11, a fourth embodiment of a locking device in accordance with the invention is depicted and is generally indicated at 111. As shown, locking device 111 is used with a conventional twin edgewise bracket 101, which includes a series of wing tips 103 projecting from a base 105. As shown, base 105 is fixed to a paid 107 that is used for attaching bracket 101 to a tooth, as previously described.

Locking device 111 is made of plastic and is somewhat similar to the locking device depicted in FIGS. 6–9. Device 111 includes a bridge 112 and a pair of depending arms 113, each of which includes a locking lip 115 for selective engagement in corresponding cut-outs 117 formed along opposite walls in base 105 of bracket 101. Locking device 111 defines a channel 119 which captures an archwire 121 retained in the archwire slot of bracket 101, as shown in FIG. 11.

Figure 12:
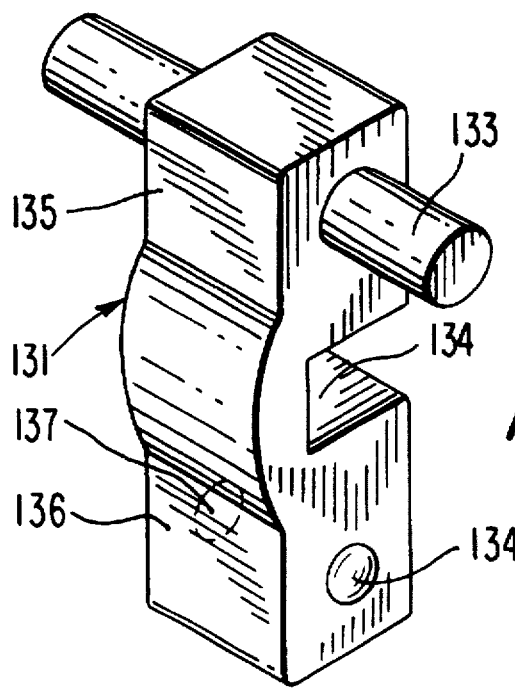
FIG. 12 is perspective view of a fifth embodiment of a locking device in accordance with the invention.

FIG. 12 depicts a fifth embodiment of the inventive locking device, which is generally indicated at 131. Locking device 131 is somewhat analogous to the locking device depicted in FIGS. 6–9 in that it includes a pivot pin 133 running through to one of arms 135, which is used for pivotally rotating device 131 from a first locked position along a dental bracket to a second unlocked position. On opposite arm 136, there is provided a pair of protruding buttons 57 which are selectively received in a corresponding pair of notches formed along the inside of the wing tips of the dental bracket. Buttons 137 facilitate the engagement of locking device 131 when it is in a locked position over the dental bracket such that the dental archwire is captured within channel 134 of locking device 131.

Figure 13:
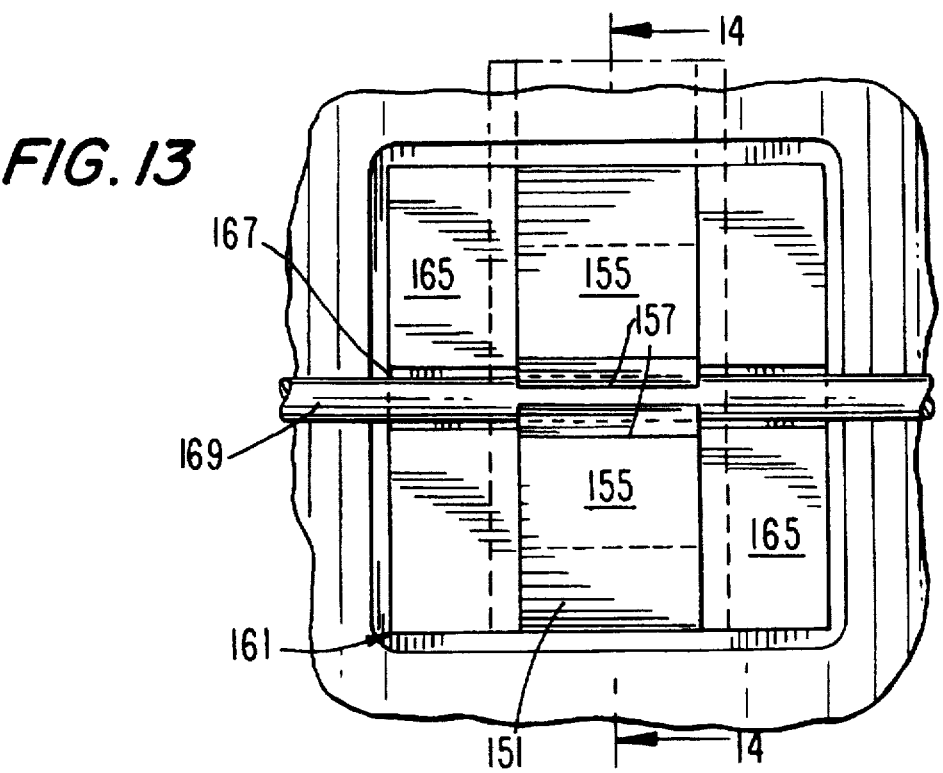
FIG. 13 is a front or top plan view of a sixth embodiment of a locking device in accordance with the invention as it is mounted on a dental bracket.
Figure 14:
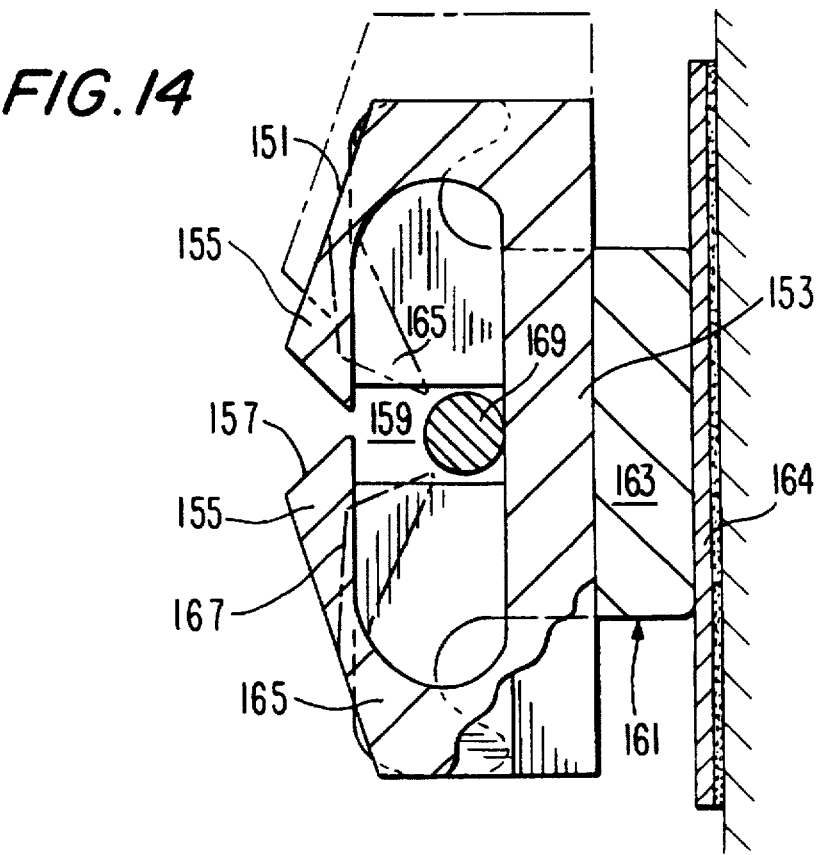
FIG. 14 is a cross-sectional view taken along line 14—14 of FIG. 13.

Turning now to FIGS. 13 and 14, a sixth embodiment of a dental locking device in accordance with the invention is now described. This embodiment of the locking device is generally indicated at 151 and is somewhat similar to the locking device depicted n FIGS. 2–5. Locking device 151 comprises a base portion 153 with a pair of upright fingers 155 extending therefrom. Each of fingers 155 includes a catch portion 157 which faces each other and which extends over opening 159 defined by fingers 155 and base 153 of locking device 151.

As with the embodiment of FIGS. 3–5, locking device 151 is slid within the channel of bracket 161 in order to capture archwire 169. As before, bracket 161 includes substantially planar base 163 and four projecting wing tips 165. Base 163 is fixed to a foil mesh pad 164 which is used for bonding bracket 161 to a tooth. Wing tips 165 define a longitudinally extending archwire slot 167 for receiving archwire 169 as shown.

As shown in FIG. 14, each of catch portions 157 of arms 155 are made of a flexible plastic material. In operation, locking device 151 is slid within the channel of bracket 161. Then, archwire 169 is positioned within opening 159 by flexing catch portions 157 of arms 155.

Figure 15:
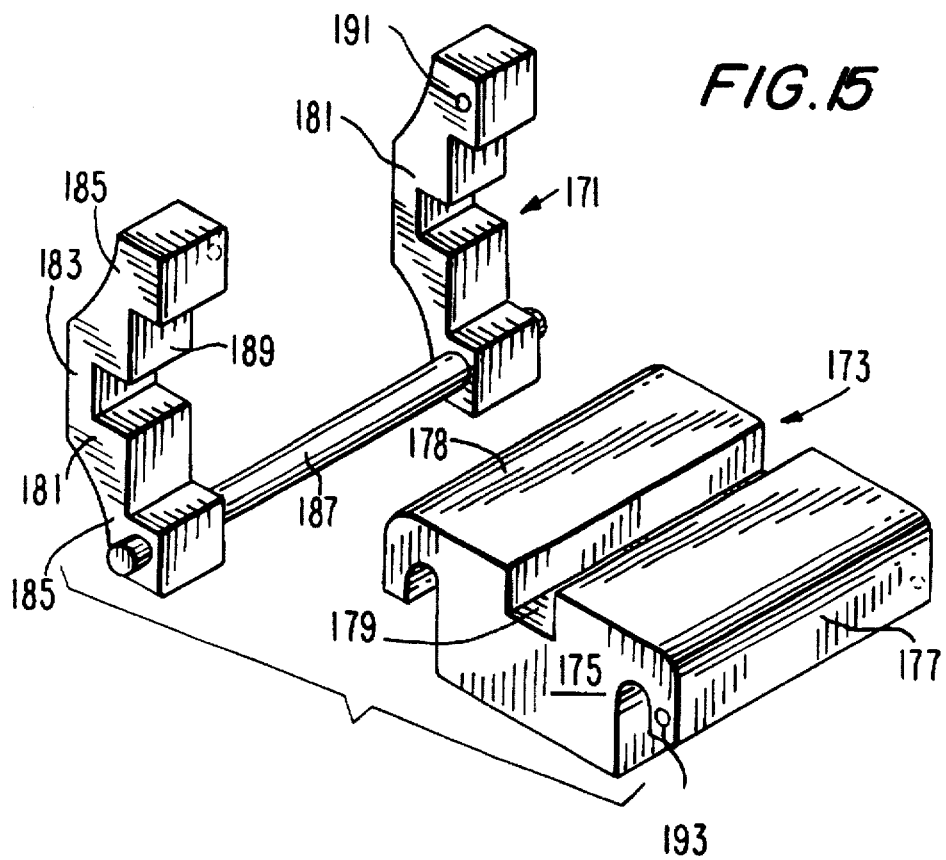
FIG. 15 is an exploded perspective view of a seventh embodiment of the inventive locking device for use with a single edgewise bracket.

Referring now to FIG. 15, a seventh embodiment of an orthodontic bracket locking device in accordance with the invention, and generally indicated at 171, is shown. Locking device 171 is used with an orthodontic single edgewise bracket, generally indicated at 173. Bracket 173 includes a substantially planar base 175 and a pair of projecting wing tips 177 and 178. As before, base 175 may be fixed to a foil mesh pad that is used for bonding bracket 173 to a tooth, as known in the art. As shown in FIG. 15, wing tips 177 and 178 define a longitudinally extending archwire slot 179 for receiving a dental archwire.

Locking device 171 includes a pair of side locking arms 181 similar in configuration to the side locking arms depicted in the embodiment illustrated in FIG. 10 and discussed hereinabove. Side locking arms 181 comprise a body 183 and a pair of arm members or fingers 185. As shown, the same corresponding arm member 185 of each of side arms 183 is fixed to the ends of a pivot pin 187. In addition, each of side locking arms 181 defines a channel 189 which is used to capture the dental archwire when locking device 171 is mounted appropriately over dental bracket 173.

In use, side locking arms 181 are positioned along the outside mesial and distal edges of wing tips 177 and 178 of single edgewise bracket 173. If positioned appropriately, pivot pin 187 is disposed underneath wing tip 178, such that channels 189 of arms 181 are aligned with archwire slot 179 in order to capture a dental archwire therein. As can be appreciated, each of arms 181 can pivotally rotate together (or separately) along pivot pin 187 in order to move locking device 171 from a first locked condition to a second unlocked condition in a manner similar to what is shown in the embodiment depicted in FIG. 10.

Continuing with FIG. 15, each of forward arm members 185 of side locking arms 181 includes an inwardly protruding button 191 which selectively mates with notches 193 formed along either side of forward wing tip 177 of bracket 173. As can be appreciated, when locking device 171 is in a locked condition, buttons 191 are engaged within notches 193 and archwire slot 179 is substantially aligned with channels 189 defined by arms 181 for capturing a dental archwire.

Figure 16:
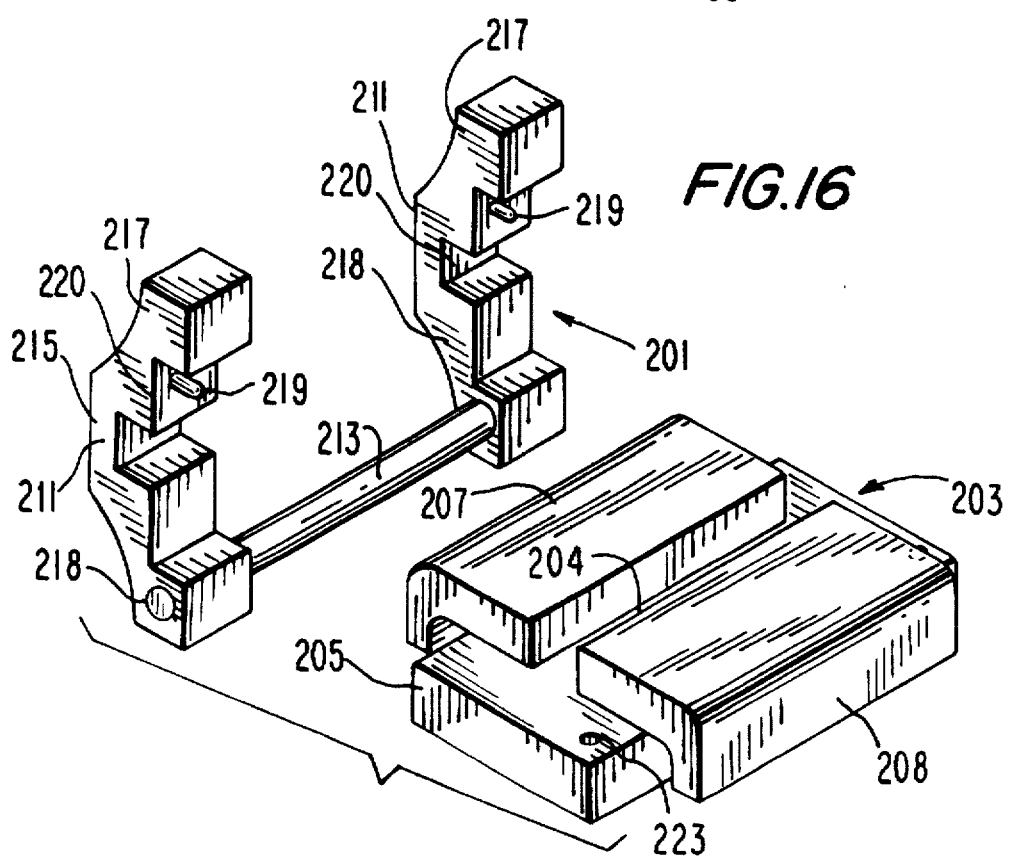
FIG. 16 is an exploded perspective view of an eighth embodiment of the inventive locking device in use with a modified single edgewise dental bracket.

In FIG. 16, an eighth embodiment of an orthodontic bracket locking device in accordance with the invention is described and generally indicated at 201. Locking device 201 is used with a second type of orthodontic single edgewise bracket, generally indicated at 203. Bracket 203 includes a substantially planar base 205 and a pair of wing tips 207 and 208. As can be appreciated, locking device 203 is different in construction from the locking device depicted in FIG. 15 in that base 205 extends past wing tips 207 and 208 on either side thereof. Wing tips 207 and 208, as before, define a longitudinally extending archwire slot 209 for receiving a dental archwire.

Locking device 201 is similar in configuration to the locking device depicted in FIG. 15, and comprises a pair of side locking arms 211 pivotally fixed to the ends of a pivot pin 213. Each of side locking arms 211 comprises a body 215 and forward and rear arm members 217 and 218 respectively, which define a channel 220 in each arm 211. Each of forward arm members 217 is formed with a depending pin at 219, which is used for engaging locking device 201 with bracket 203, as described below.

In operation, side locking arms 95 are positioned outside the mesial and distal edges of wing tips 207 and 208 of bracket 203, and pivot pin 213 is disposed underneath wing tip 207. In such mounting, locking arms 211 are disposed over the extending outside edges of base 205, such that each of channels 220 defined by arms 211 is substantially aligned with archwire slot 209. As with the embodiment depicted in FIG. 15, each of arms 211 is enabled to rotate together along pivot pin 213 in order to move locking device 201 from a first locked condition to a second unlocked condition. In a locked condition, pins 219 of arm member 217 engage with pin holes 223 formed within base 205 along either side thereof. This engagement between pins 219 and holes 223 facilitates the locking of locking device 201 within dental bracket 203.

Figure 17:
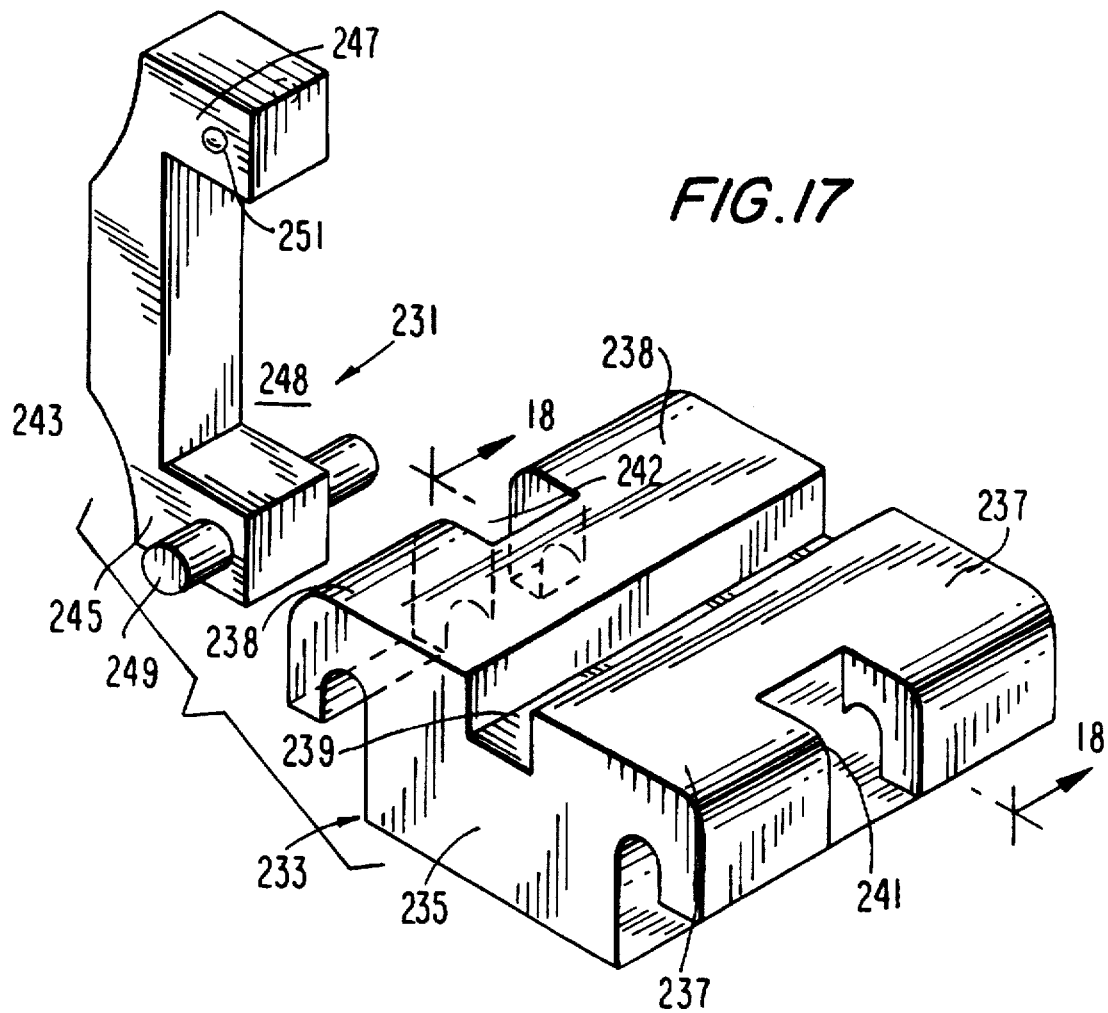
FIG. 17 is an exploded perspective view of a ninth embodiment of the inventive locking device for use with a modified twin edgewise dental bracket.
Figure 18:
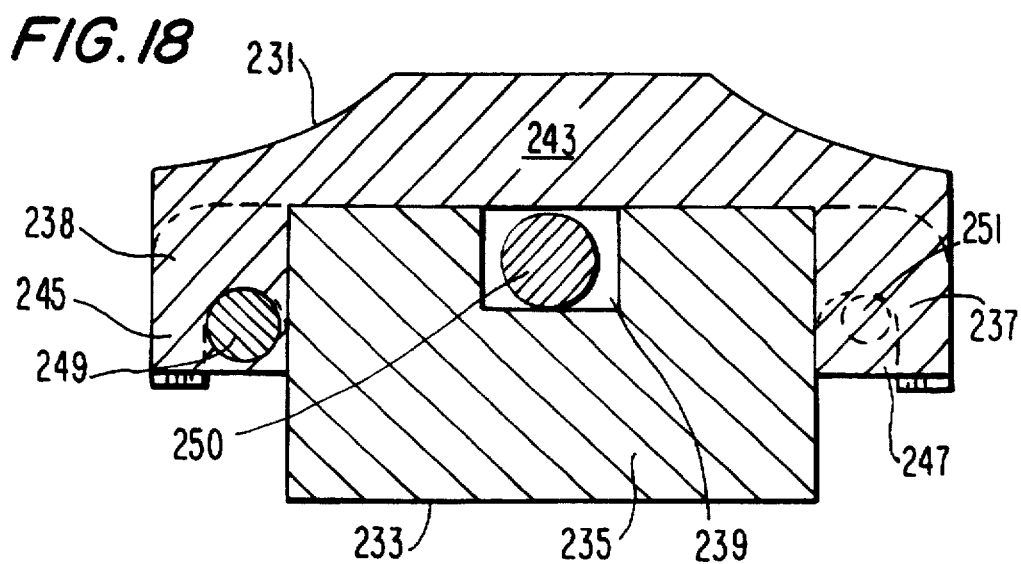
FIG. 18 is a cross-sectional view taken along line 18—18 of FIG. 17.

Turning now to FIGS. 17 and 18, a ninth embodiment of an orthodontic bracket locking device, in accordance with the invention and generally indicated at 231, is shown. Locking device 231 is here used with a modified orthodontic twin edgewise bracket, generally indicated at 233. Bracket 233 is somewhat similar to the twin edgewise brackets depicted in the earlier embodiments, and includes a substantially planar base 235, and four projecting flexible wing tips 237 (two forward and two rear). Wing tips 237 and 238 define a longitudinally extending archwire slot 239 for receiving a dental archwire. Wing tips 237 and 238 further define a pair of laterally extending forward and rear cut-outs 241 and 242 respectively, which receive locking device 231, as described below.

Locking device 231 comprises a base portion 243, with a pair of fingers 245 and 247 extending therefrom. Fingers 245 and 247 define a cut-out 248 therebetween which is used for retaining an archwire 250 within archwire slot 239 when locking device 231 is mounted over bracket 233. Finger 245 receives therethrough a pivot pin 249 for enabling locking device 231 to selectively pivotally rotate. Finger 247 is formed with a pair of side protrusions or buttons 251 for selective engagement underneath forward wing tips 237, as best shown in FIG. 18.

In operation, locking device 231 can rotate along pivot pin 249, which is disposed underneath rear wing tips 238 (see FIG. 18), from a first unlocked condition to a second locked condition. In a locked condition, as shown in FIG. 18, cut-out 248 of device 231 captures archwire 250 therewithin when locking device 231 is in a locked condition. At the same time, finger 247 of locking device 241 is pushed through forward cut-out 241 defined by wing tips 237 until protrusions 251 engage wing tips 237 thereunder.

As can be appreciated, the locking device of the invention is advantageous since it is selectively removable from engagement within a traditional single or twin edgewise bracket. As a result, the dental practitioner may conduct further treatment using a steel or elastomeric ligature.

Both the bracket and the locking device of the invention may be made from molded plastic or metal, and may be prepared by using powdered injection molding.

It will thus be seen that the objects set forth above, among those made apparent from the preceding description, are efficiently attained, and since certain changes may be made in the product described herein, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

I claim:

1. An orthodontic system comprising:
   a twin edgewise bracket for engagement with a tooth, said bracket comprising a base which leads into two pairs of wing tips with each pair depending from either side of said base, and thereby defining a longitudinal at least partially continuous groove running between said pairs, each of said pairs further defining a laterally continuous extending slot for selectively receiving an orthodontic archwire; and
   an archwire locking device for maintaining said archwire within said laterally extending slot, said locking device being pivotally rotatable between a first locked position within said longitudinal groove and between said wing tip pairs for capturing said archwire, and a second unlocked position away from said longitudinal groove;
   said locking device being pivotally rotatable by means of a pivot pin connected thereto and removably disposed underneath one of said pairs of wing tips.

2. The system of claim 1, further including means for locking said locking device within said bracket when said locking device is in a locked condition.

3. The system of claim 2, wherein said locking means includes at least one button disposed along said locking device and at least one corresponding notch formed along said bracket in which said at least one button is selectively engaged.

4. The system of claim 3, wherein at least one wing tip from said wing tip pairs includes said at least one notch for selective engagement with said at least one button of said locking device.

5. The system of claim 2, wherein said locking device includes at least one protruding lip for engaging at least one notch running along the base of said bracket.

6. The system of claim 1, wherein said locking device encloses said archwire in said extending slot when said device is in said locked condition.

7. The system of claim 6, wherein said locking device includes a pair of arms for defining a locking slot therebetween.

8. The system of claim 7, wherein said archwire is captured in said locking slot when said locking device is in a locked condition.

9. The system of claim 8, wherein one of said arms is connected to said pivot pin for enabling said device to pivotally rotate.

10. The system of claim 1, further including means for locking said locking device within said bracket when said locking device is in a locked condition.

11. For a twin edgewise dental bracket having two pairs of opposite sided wing tips with a laterally extending slot and a longitudinally extending groove, a removable locking device for maintaining a dental archwire within said slot, said locking device comprising a pair of arms defining a locking slot therebetween, said device being sized to pivotally move between a first locked position along said bracket and within said groove such that said locking slot is substantially aligned with said extending slot so as to enable capture of said archwire, and a second unlocked position such that said slots are not aligned and said archwire is free from capture by said locking device.

12. The device of claim 11, further including means for locking said device along said bracket when said device is in a locked condition.

13. The device of claim 11, further including a bridge disposed between said arms for enclosing said archwire within said extending slot.

14. The device of claim 11, wherein one of said arms has a connected pivot pin sized to be removably disposed underneath one of said wing tip pairs for enabling said device to fully rotate between a locked condition and an unlocked condition.

15. The device of claim 14, further including a pair of pivotally rotatable side locking arms.

16. An orthodontic system comprising:
at least one edgewise bracket for engagement with a tooth, said bracket comprising a base which leads into at least a pair of wing tips for defining a laterally extending slot for selectively receiving an orthodontic archwire; and
an archwire locking device for maintaining said archwire within said laterally extending slot, said locking device being pivotally rotatable between a first locked position and a second unlocked position.

17. An orthodontic system comprising:
at least one twin edgewise bracket for engagement with a tooth, said bracket comprising a base which leads into two pairs of wing tips with each pair depending from either side of said base, and thereby defining a longitudinal at least partially continuous groove running between said pairs, each of said pairs further defining a laterally continuous extending slot for selectively receiving an orthodontic archwire;
an archwire locking device for maintaining said archwire within said laterally extending slot, said locking device being pivotally rotatable between a first locked position within said longitudinal groove and between said wing tip pairs for capturing said archwire, and a second unlocked position away from said longitudinal groove; and
a locking mechanism for locking said locking device within said bracket when said locking device is in a locked condition comprising at least one button disposed along said locking device and at least one corresponding notch formed along said bracket in which said at least one button is selectively engaged.

18. An orthodontic system comprising:
at least one twin edgewise bracket for engagement with a tooth, said bracket comprising a base which leads into two pairs of wing tips with each pair depending from either side of said base, and thereby defining a longitudinal at least partially continuous groove running between said pairs, each of said pairs further defining a laterally continuous extending slot for selectively receiving an orthodontic archwire;
an archwire locking device for maintaining said archwire within said laterally extending slot, said locking device being pivotally rotatable between a first locked position within said longitudinal groove and between said wing tip pairs for capturing said archwire, and a second unlocked position away from said longitudinal groove;
a locking mechanism for locking said locking device within said bracket when said locking device is in a locked condition comprising a protruding lip disposed along one end of said locking device for selective engagement with a notch formed along said base of said bracket.

19. An orthodontic system comprising:
at least one twin edgewise bracket for engagement with a tooth, said bracket comprising a base which leads into two pairs of wing tips with each pair depending from either side of said base, and thereby defining a longitudinal at least partially continuous groove running between said pairs, each of said pairs further defining a laterally continuous extending slot for selectively receiving an orthodontic archwire; and
an archwire locking device for maintaining said archwire within said laterally extending slot, said locking device being pivotally rotatable between a first locked position along said longitudinal groove and between said wing tip pairs for capturing said archwire, and a second unlocked position away from said longitudinal groove;
wherein said locking device comprises a pair of side locking arms pivotally rotatable from said first position to said second position.

20. The locking device of claim 19, wherein said locking device further includes a central locking member.

21. The system of claim 20, wherein said locking device encloses said archwire in said extending slot when said device is in a locked condition.

22. The system of claim 21, wherein said locking device includes a pair of fingers for defining a locking slot therebetween.

23. The system of claim 22, wherein said archwire is captured in said locking slot when said locking device is in a locked condition.

24. The system of claim 22, wherein one of said fingers of said locking device includes at least one protruding member for selectively engaging at least one opening formed in said bracket.

25. The system of claim 20, further including means for locking said locking device within said bracket when said locking device is in a locked condition.

26. The system of claim 25, wherein said locking means includes at least one button disposed along said locking device and at least one corresponding notch formed along said bracket in which said at least one button is selectively engaged.

27. The system of claim 26, wherein at least one of said wing tips includes said at least one notch for selective engagement with said at least one corresponding button formed in said device.

28. The system of claim 20, wherein said locking device comprises a pair of side locking arms pivotally connected to a pivot pin extending therebetween.

29. The system of claim 28, wherein said pivot pin is sized to fit underneath at least one of said wing tips.

30. The system of claim 28, wherein each of said locking arms includes a pair of fingers for defining a locking slot therebetween.

31. The system of claim 28, wherein said archwire is captured in said locking slots of said side locking arms when said locking device is in a locked condition.

32. An orthodontic system comprising:
- an edgewise bracket for engagement with a tooth, said bracket comprising a base which leads into at least a pair of wing tips for defining a laterally extending slot for selectively receiving an orthodontic archwire; and
- an archwire locking device for maintaining said archwire within said laterally extending slot, said locking device being pivotally rotatable between a first locked position for enclosing said archwire in said extending slot and a second unlocked position;

wherein said locking device includes a pivot pin for enabling said locking device to pivotally rotate, said pivot pin being sized to fit underneath at least one of said wing tips, and further being selectively and freely removable from underneath said at least one of said wing tips.

* * * * *